United States Patent
Burkhart

(10) Patent No.: US 7,981,140 B2
(45) Date of Patent: Jul. 19, 2011

(54) KNOTLESS FIXATION OF TISSUE TO BONE WITH SUTURE CHAIN

(75) Inventor: Stephen S. Burkhart, San Antonio, TX (US)

(73) Assignee: Arthrex, Inc., Naples, FL (US)

( * ) Notice: Subject to any disclaimer, the term of this patent is extended or adjusted under 35 U.S.C. 154(b) by 1199 days.

(21) Appl. No.: 11/702,621

(22) Filed: Feb. 6, 2007

(65) Prior Publication Data
US 2007/0135843 A1   Jun. 14, 2007

Related U.S. Application Data

(63) Continuation-in-part of application No. 11/392,798, filed on Mar. 30, 2006, now Pat. No. 7,803,173.

(60) Provisional application No. 60/666,518, filed on Mar. 30, 2005.

(51) Int. Cl.
*A61B 17/04* (2006.01)
*A61B 17/84* (2006.01)

(52) U.S. Cl. .................................. 606/232; 606/300

(58) Field of Classification Search .............. 606/232, 606/300, 301, 213, 215, 216, 139, 144
See application file for complete search history.

(56) References Cited

U.S. PATENT DOCUMENTS

| 5,891,168 A * | 4/1999 | Thal ........................ 606/232 |
| 6,143,017 A | 11/2000 | Thal |
| 6,838,493 B2 * | 1/2005 | Williams et al. ........ 606/300 |
| 7,585,311 B2 * | 9/2009 | Green et al. ............. 606/232 |

* cited by examiner

Primary Examiner — Julian W Woo
(74) Attorney, Agent, or Firm — Dickstein Shapiro LLP

(57) ABSTRACT

A chain of loops of braided high strength suture for soft tissue to bone fixation. The suture chain is advantageous for use in knotless fixation of soft tissue to bone, and can be used for knotless side-to-side suturing of U-shaped defects, such as rotator cuff tears. The soft tissue to bone fixation includes: (i) providing a first medial row constructed with a first plurality of fixation devices, at least one of the first plurality of fixation devices being an anchor; (ii) providing a second lateral row constructed with a second plurality of fixation devices, at least one of the second plurality of fixation devices being a knotless fixation device; (iii) providing a suture loop construct that includes at least two loops formed of and connected by suture; and (iv) fixating the suture loop construct so that it extends over the soft tissue and is secured in place by at least one of the fixation devices or anchors.

11 Claims, 18 Drawing Sheets

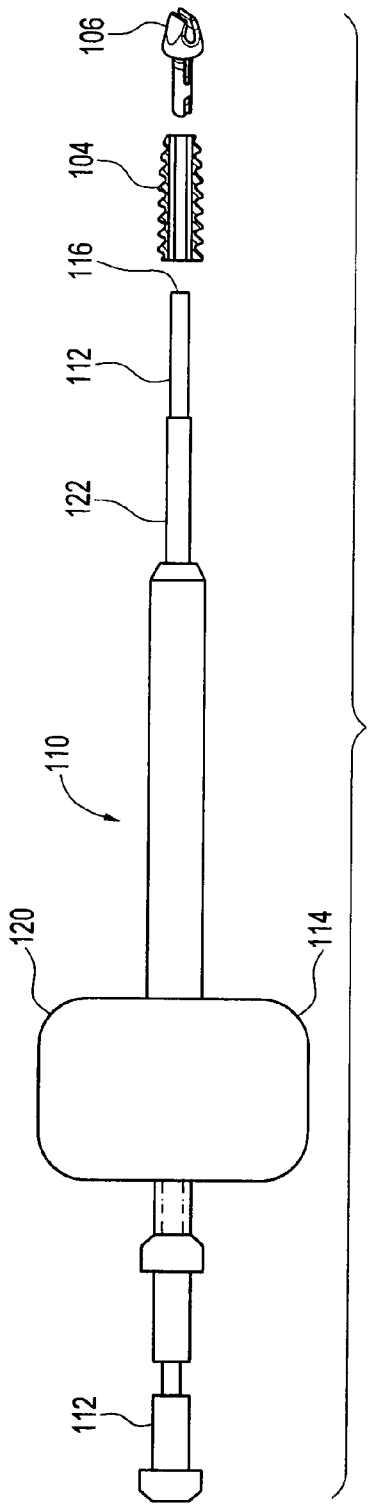
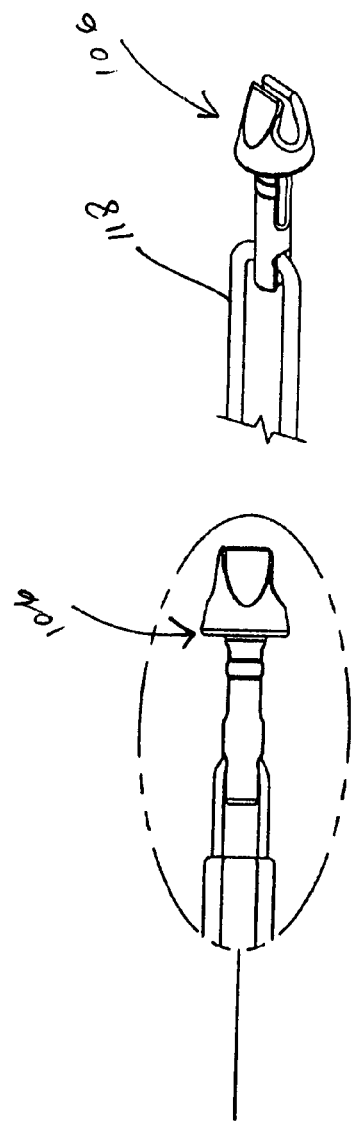
FIG. 21
FIG. 21A
FIG. 21B

KNOTLESS FIXATION OF TISSUE TO BONE WITH SUTURE CHAIN

CROSS-REFERENCE TO RELATED APPLICATIONS

This application is a continuation-in-part application of U.S. application Ser. No. 11/392,798, filed on Mar. 30, 2006 now U.S. Pat. No. 7,803,173, which in turn claims the benefit of U.S. Provisional Application Ser. No. 60/666,518, filed on Mar. 30, 2005, the entire disclosures of which are incorporated by reference herein.

BACKGROUND OF THE INVENTION

1. Field of the Invention

The present invention relates to surgical fixation and, more particularly, to knotless fixation of tissue to bone using a chain-like serial suture loop construct.

2. Description of the Related Art

Securing suture during surgery can be difficult and demanding. Various suture constructs have been developed in an effort to avoid the need to tie knots in suture, particularly during arthroscopic surgery. For example, U.S. Pat. No. 6,143,017 to Thal discloses tissue fixation using a free-standing continuous suture loop snagged by an anchoring device. While it appears that tissue can be bound to bone according to the Thal teachings, it is not evident how to accomplish in situ surgical refinements such as adjustment of the loop length or tension on the repaired tissue. Technology for knotless tissue fixation would benefit from further development.

SUMMARY OF THE INVENTION

The present invention provides apparatus and methods for knotless tissue fixation using serial suture loop constructs. The construct preferably includes at least two loops formed of high strength suture. The suture loop constructs allow for surgical fixation of tissue without the need to tie knots. The loops are captured with anchoring implants. Tension on the fixation can be refined in situ by selecting which loops to capture.

The present invention also provides a method for knotless fixation of anatomical tissue during surgical applications by employing a chain of suture loops. The method comprises the steps of: (i) providing a construct that includes at least two loops formed of and connected by suture; and (ii) surgically fixating the anatomical tissue using the suture loop construct without tying knots.

The present invention further provides a method for tendon to bone fixation which includes: (i) providing a first medial row constructed with a first plurality of fixation devices, at least one of the first plurality of fixation devices being an anchor; (ii) providing a second lateral row constructed with a second plurality of fixation devices, at least one of the second plurality of fixation devices being a knotless fixation device; (iii) providing a suture loop construct that includes at least two loops formed of and connected by suture; and (iv) fixating the suture loop construct so that it extends over the soft tissue and is secured in place by at least one of the fixation device of the anchors.

The present invention additionally provides a method of tensioning suture used for knotless fixation of anatomical tissue during surgical applications. The method includes the steps of: (i) providing a suture chain that includes at least two loops formed of high strength suture; (ii) securing an end of the suture chain to a fixation device; and (iii) pulling on the other end of the suture chain to tension the suture chain.

Other features and advantages of the present invention will become apparent from the following description of exemplary embodiments of the invention with reference to the accompanying drawings.

BRIEF DESCRIPTION OF THE DRAWINGS

FIG. 21 is an exploded view of a two-part driver for the swivel suture chain anchor shown in FIG. 18;

FIGS. 21A and 21B are enlarged views of the forked tip of the swivel suture chain anchor shown in FIG. 21;

DETAILED DESCRIPTION OF THE INVENTION

Figure 1:
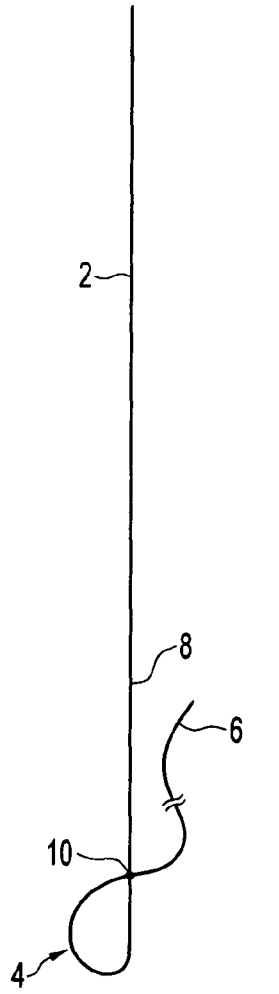
FIG. 1 illustrates an initial stage of chained suture loop formation according to the present invention.

The present invention provides apparatus and methods for knotless tissue fixation using serial suture loop constructs. The construct preferably includes at least two loops of suture, preferably high strength suture. The suture loop constructs allow for surgical fixation of tissue without the need to tie knots. The loops are captured with anchoring implants or similar devices.

The invention also provides a method of forming a chain of suture loops, preferably of braided high strength suture loops, for surgical applications. As described in more detail below, the suture chain can comprise a series of closed loops of suture formed in a conventional "chain." Alternatively, at least one of the loops or "links" of the chain can be formed first by "piercing" or "lacing" an end of the suture through a standing part of the suture, to form an initial suture "intersection" in a first direction (for example, in the x-y direction). The suture intersection is then locked by lacing the end through the suture intersection in a second direction (for example, in the z direction), piercing both strands at the center of the initial junction, and pulling the strands tight. Successive loops or links may be developed along the length of suture in similar fashion to form a suture chain.

Suture loop constructs according to the present invention are referred to as "chains" in this application. The term "chain" is used in the specification and claims to refer to exemplary embodiments of the invention. A "chain" in this context refers broadly to a construct including a series of loops. The loops can be, but need not be, interlinked. In this manner, the term "chain" as used in this application includes, but need not be limited to, the commonly understood definition in which links or rings are fitted into one another. Rather, the chains of the present invention can include two or more loops that are connected together.

Each loop preferably has a fixed perimeter. The suture can be interlaced, rather than knotted, as described further below, to establish and maintain loop geometry. Preferably, all loops are similar in size.

In an exemplary embodiment, high-strength suture is utilized, such as the high strength suture sold by Arthrex, Inc. of Naples, Fla. under the tradename FiberWire, which is disclosed and claimed in U.S. Pat. No. 6,716,234, the entire disclosure of which is incorporated herein by reference.

FiberWire suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire suture includes a core within a hollow braided construct, the core being a twisted yarn of UHMWPE. The suture may optionally include filaments of various colors.

Suture chains of the present invention incorporating advanced, high strength materials, such as FiberWire suture, can be used in demanding orthopedic applications such as shoulder repairs. The suture chains of the present invention offer surgeons practical means for creating suture constructs of adjustable size without having to tie a knot in situ.

Referring now to the drawings, where like elements are designated by like reference numerals, FIG. 1 illustrates a length of suture 2 at an initial stage of suture chain formation according to one embodiment of the present invention. A first suture loop 4 is formed by lacing suture 2 through itself at least once, preferably at least twice. Using a 0.029" or smaller needle, for example, loop 4 is started by lacing a bitter end 6 of the suture 2 between filaments of a standing part 8 of suture 2 to establish a junction 10. Thus, junction 10 is formed initially as a four-way intersection of suture 2 laced through itself.

Junction 10 is sufficient to establish a suture loop, and the present invention includes looped constructs formed in the above manner. It is preferable, however, to "lock" the junction 10 to establish a fixed size. The junction 10 can be locked in various ways, including wrapping junction 10 with suture, tying a knot around junction 10, or by applying adhesive to junction 10.

Figure 2:
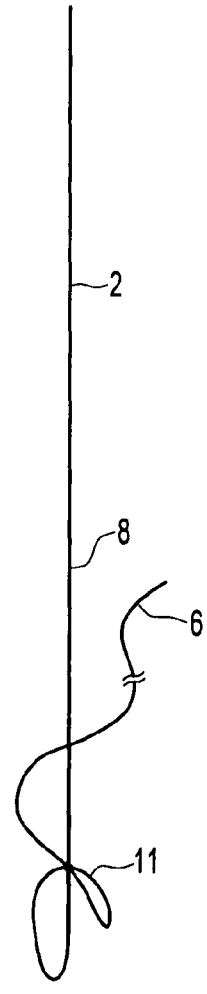
FIG. 2 illustrates locking a suture loop and initial formation of an adjacent loop on the chain according to the present invention.
Figure 3:
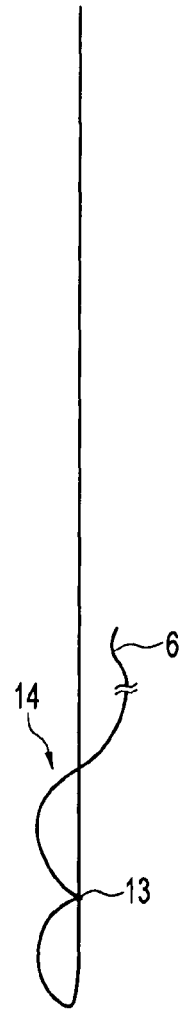
FIG. 3 illustrates formation of the adjacent loop of the chained suture loops according to the present invention.
Figure 5:
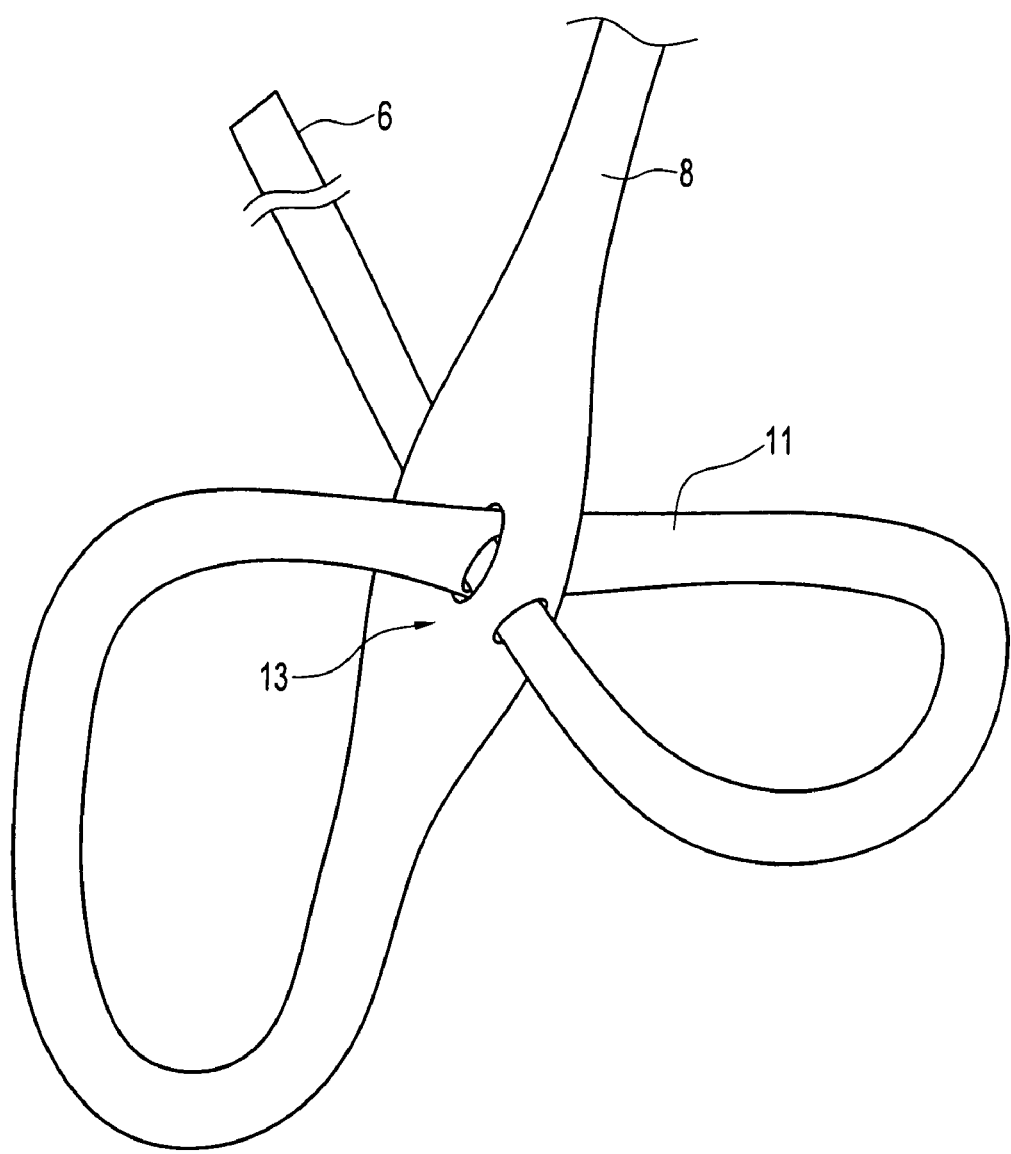
FIG. 5 provides an enlarged depiction of suture loop formation according to an exemplary embodiment of the present invention.

In an exemplary embodiment of the present invention, junction 10 is locked by lacing the suture through itself again, as follows: Referring to FIGS. 2 and 3, bitter end 6 again is laced (using a needle, not shown) through the previously-interlaced standing parts 8, 11 of suture 2 at junction 10. As a result, a six-way intersecting junction 13 of suture 2 is formed. Locking of the twice-interlaced junction 13 is completed by pulling suture 2 tight, as shown in FIG. 3. FIG. 5 is an enlarged view of junction 13 prior to tightening.

FIG. 3 also shows initial development of a second suture loop 14 formed by lacing bitter end 6 through standing part 8 of suture 2 to form a two-way junction 16 similar to junction 10. The junction 16 is locked as described above for the first loop 4. The second loop 14 preferably is the same size as the first loop 4.

Figure 4:
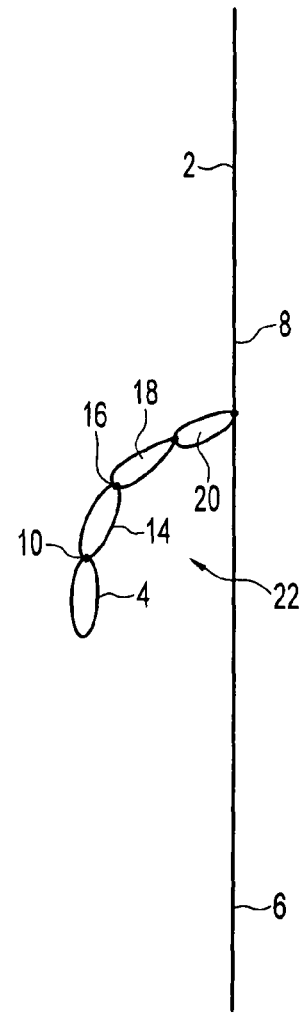
FIG. 4 illustrates a completed suture loop chain according to the present invention.

Referring to FIG. 4, the steps described above are repeated to produce additional loops 18, 20. Thus, a chain of suture loops 22 is formed with four loops 4, 12, 18, 20. Suture loop chain 22 can have fewer or more than the four loops shown in FIG. 4. Although shorter chains, having two or three loops, often are preferred for working arthroscopically, the appropriate length will be determined as required by the intended application.

Alternative methods of forming a chain of suture loops without tying knots is described as follows: The junction 10 is formed by crossing suture 2 over or under the standing part 8. The bitter end 6 is then passed through the two overlapping portions of suture to secure the loop. The resulting junction is less stable than the twice interlaced junction 13 achieved by the method first described above, however. As a further alternative, various knots known to those of skill in the art could be used alone, or could be combined with interlacing as described above, to form any or all of the loops. Fixed loops are preferred, although an adjustable loop construct could be provided within the bounds of the teachings of the present invention. Twice-interlaced junctions, such as those first described above in connection with junction 13, are most preferred. These junctions maintain the loop geometry well, present a smoother outer surface, and may involve less suture weakening than do knots.

Figure 5A:
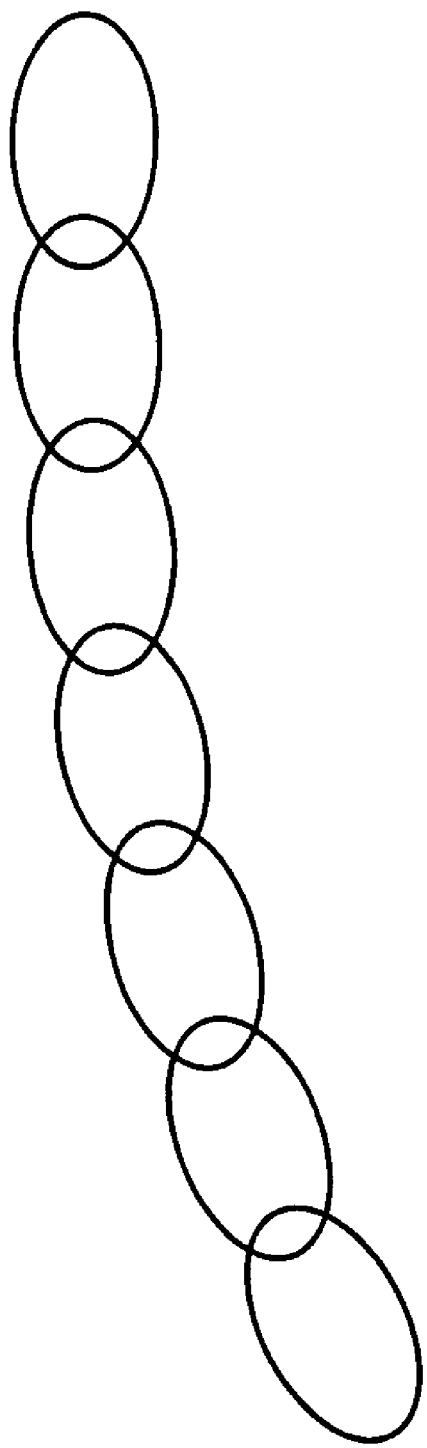
FIG. 5A shows a suture chain of the present invention as conventional configuration of a series of interconnected loops.

Alternatively, as shown in FIG. 5A, the suture chain of the present invention can simply comprise a series of interconnected suture loops, in the more conventional "chain" configuration.

Figure 6:
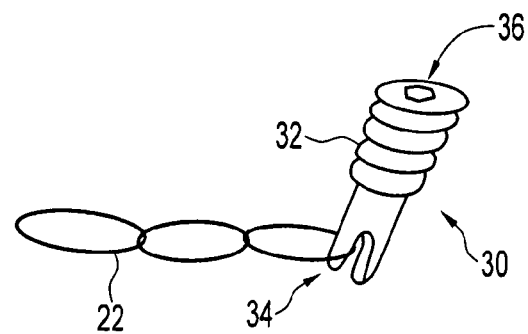
FIG. 6 illustrates a press-in suture chain anchor according to the present invention.
Figure 7:
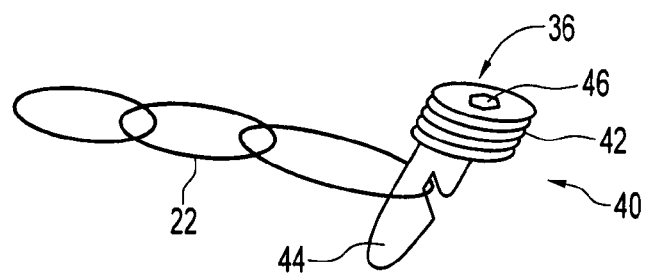
FIG. 7 illustrates an alternative suture chain anchor of the present invention.
Figure 8:
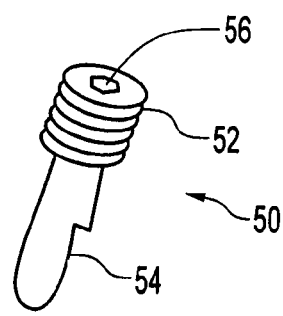
FIG. 8 illustrates a third alternative suture chain anchor according to the present invention.

The suture chains of the present invention can be used in a variety of surgical procedures, and most preferably are used to approximate tissue, for example, to approximate torn tendons to bone. FIGS. 6-8 illustrate examples of bone anchors used to secure one or more suture chains to bone in accordance with the present invention. In FIG. 6, a forked suture anchor 30 has a threaded body 32. A loop of the suture chain 22 is hooked between tines of forked tip 34. The anchor 30 is installed into bone using a hex driver received in hex socket 36, for example.

FIG. 7 illustrates a notched suture chain anchor 40 having a threaded body 42, a tip 44 notched on one side, and a hex socket 46. A loop of suture chain 22 is shown captured in the side notch. Although an end loop is shown here as the one being captured, the invention is not so limited. FIG. 8 illustrates a shouldered suture chain anchor 50 having a threaded body 52, a shouldered tip 54, and a hex socket 56. Alternatively, each of the anchors 30, 40, 50 can be provided with a tip 34, 44, 54 that is rotatably attached to its respective body 32, 42, 52, as described further below. Other types of bone anchors can also be used, without limitation. Although threaded anchors are shown, swivel anchors (described below) or press-in anchors such as the Arthrex Push-Lock™ anchor described in U.S. Patent Application Publication No. 2004/0093031, the disclosure of which is incorporated by reference herein, can be used as well. Also, rather than capturing a loop with the anchor, the chain of loops can be threaded through the eye of a needle or bone anchor, for example. The use of a bone anchor also is not necessary to utilizing suture chains of the present invention.

Figure 9:
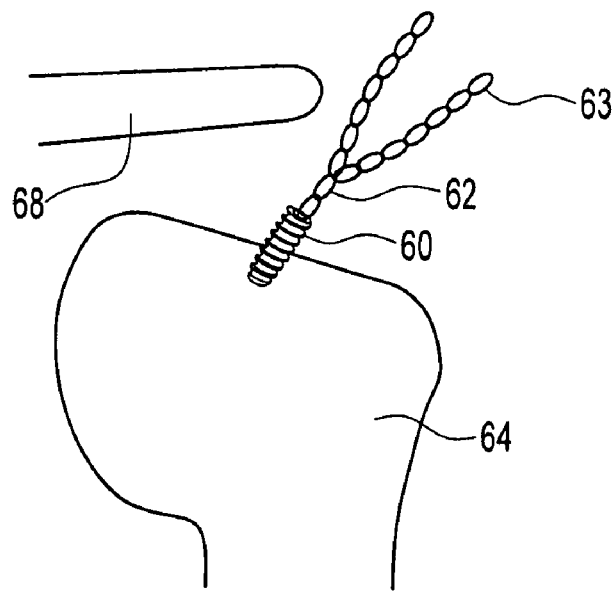
FIG. 9 depicts an initial step in shoulder repair using a double-row technique according to the present invention.
Figure 10:
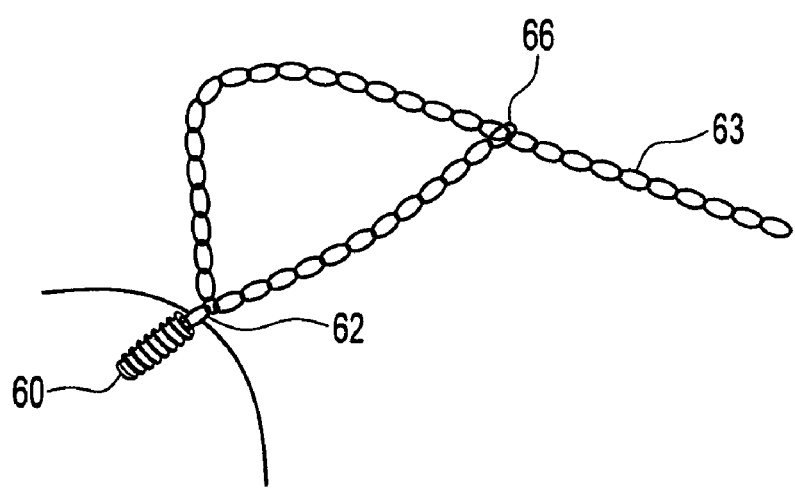
FIG. 10 depicts a step of securing the suture chain to the bone anchor according to the present invention.
Figure 11:
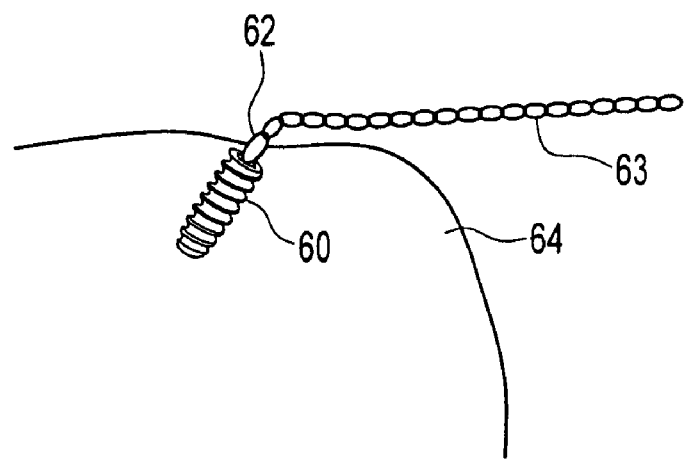
FIG. 11 depicts a step of tightening the suture chain onto the bone anchor according to the present invention.

Method steps of tissue fixation according to an exemplary embodiment of the present invention are depicted schematically in FIGS. 9-14. Referring initially to FIG. 9, a suture anchor 60 (for example, an Arthrex Biocorkscrew™, disclosed in U.S. Patent Application Publication No. 2004/0106950) having an eyelet 62 and loaded with a single or double strands of suture chain 63 is installed in bone 64. As shown in FIG. 10, with the suture chain 63 threaded through eyelet 62 of suture anchor 60, one end of suture chain 63 is passed through a loop, such as the last loop 66, of suture chain 63. Referring to FIG. 11, suture chain 63 is tightened so that link 66 is drawn adjacent eye 62 of anchor 60, and a single suture chain leg 63 extends from eyelet 62 of anchor 60.

Figure 12:
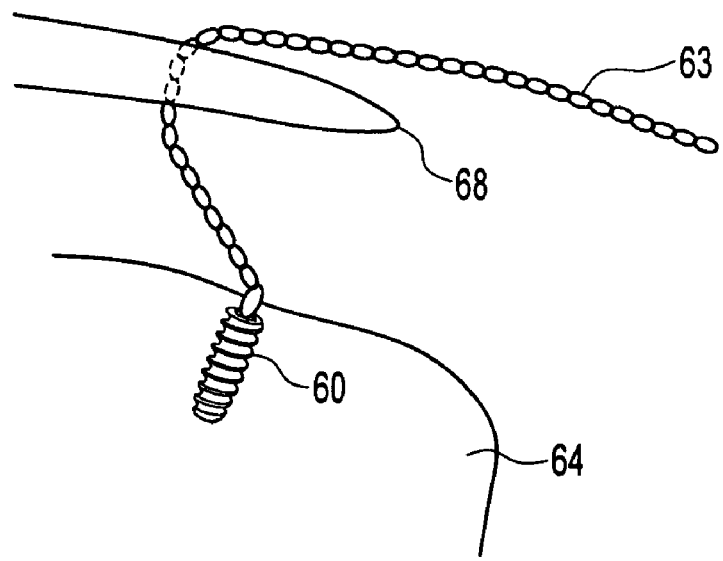
FIG. 12 depicts a step of passing the suture chain through a tendon to be reattached to bone according to the present invention.
Figure 13:
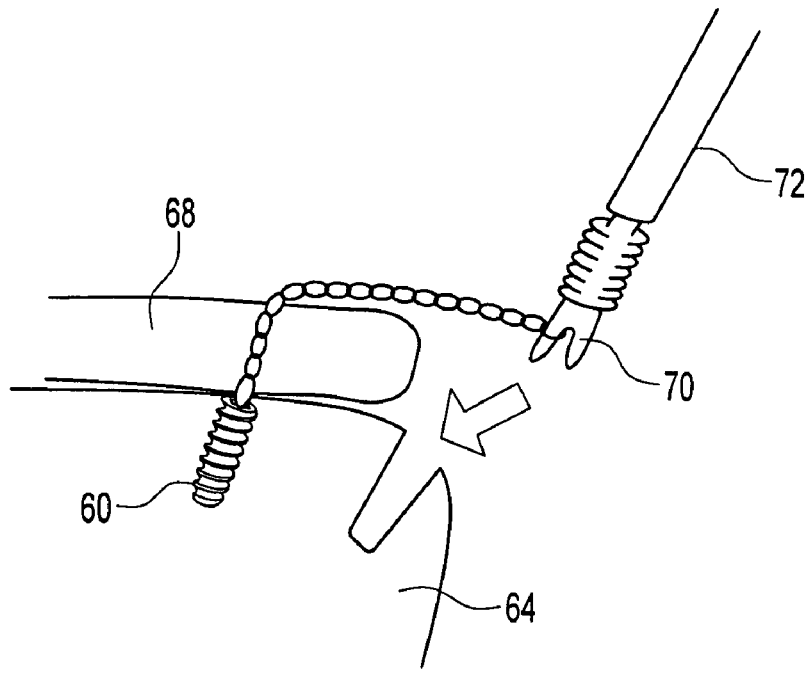
FIG. 13 depicts a step of tendon fixation by installing a suture chain anchor according to the present invention.
Figure 14:
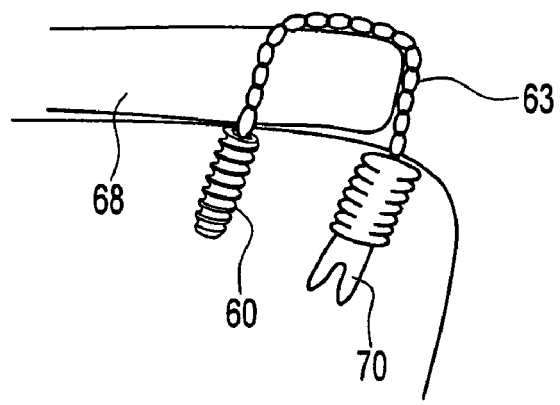
FIG. 14 depicts a completed tendon repair using a suture chain according to the present invention.

Referring next to FIG. 12, once the suture anchor has been inserted, suture chain 63 is passed through tendon 68. As shown in FIG. 13, tissue 68 is approximated to bone 64 using a second suture anchor 70. In an exemplary embodiment, second suture anchor 70 is installed using a driver 72 into a preformed opening in bone 64, with a selected loop of suture chain 63 having been captured (on the prong of the anchor) to provide the desired tension on the finished construct, shown in FIG. 14. Assorted bone anchors 60, 70 could be substituted for suture chain anchors 60, 70. The suture anchor may be an Arthrex SwiveLock™ (swivel suture anchor) described below, or an Arthrex Push-Lock™ anchor. Alternatively, the suture chain passed through the tissue can be secured using a single anchor. In addition, various anchors, such as those noted above and others, may be used interchangeably with only slight variations in the above procedure. For example, the suture chain can be secured by capturing two of the chain loops in forked tines prior to insertion of the anchor or anchors.

Further, regular suture may be used in addition to the suture chains of the present invention. In this case, the first suture anchor 60 will be pre-loaded with regular suture (like the current Arthrex BioCorkscrew™ or Arthrex BioCorkscrew-FT™, disclosed in U.S. Ser. No. 11/224,060). In this exemplary embodiment, the technique is similar to the one described above, except that the lateral fixation is accomplished by capturing the suture limbs (rather than chain-links) in the fork of the SwiveLock™ and tensioning the suture as the SwiveLock™ is placed. This relies on interference fixation of the suture between the anchor and the bone.

Greater fixation may be achieved by twisting the suture limbs before inserting the anchor. For the suture chain of the present invention, tension is adjusted simply by choosing to capture a different link. That is, a link is chosen and pushed to the bottom of the bone socket by the driver. If the soft tissue is not firmly held against bone, the inserter is withdrawn and a more proximal link is chosen. This gives great freedom to adjust the tension in the system.

Figure 15:
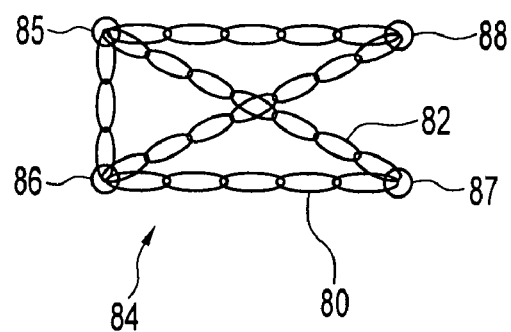
FIG. 15 illustrates a shared-load fixation using a suture chain according to the present invention.

Suture chains disclosed herein also can be used to increase the footprint of a repair and to share repair loading. Referring to FIG. 15, suture chain(s) 80, 82 are depicted in a construct fixing a section of tissue 84 to underlying bone (not shown). Using two lengths of suture chain (the second length 82 could be separately formed, or an extension of suture chain 80) provides load sharing and increases the construct footprint. Suture chains 80, 82 can be secured to bone by lacing the suture chains 80, 82 through tissue 84 at points 85, 86, 87, 88 in various patterns using four or fewer bone anchors.

Figure 16:
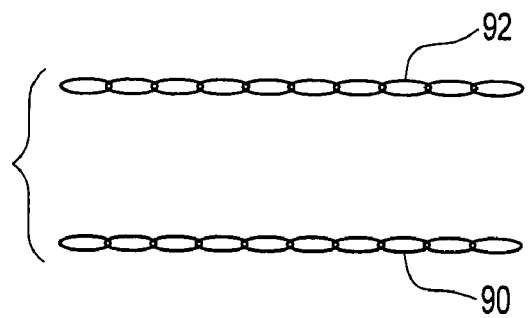
FIG. 16 illustrates an unacceptably loose tissue approximation using a suture chain construct of the present invention.
Figure 17:
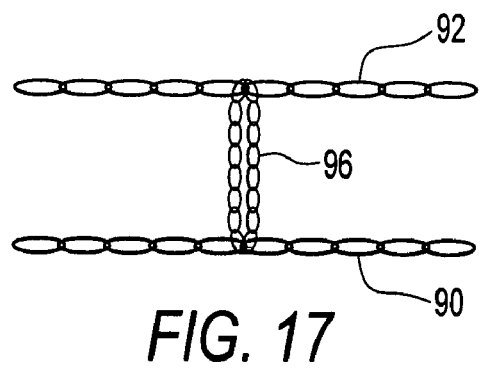
FIG. 17 illustrates a method of tightening the loose suture chain approximation according to the present invention.

Referring to FIG. 16, two suture chains 90, 92 are attached through tissue 94 to underlying bone (not shown) in a tissue-approximating construct. Suture chains 90, 92 have unacceptable laxity. Referring to FIG. 17, a length of suture chain 96 is looped around suture chains 90, 92, or through individual loops of suture chains 90, 92 to tighten the construct.

Figure 18:
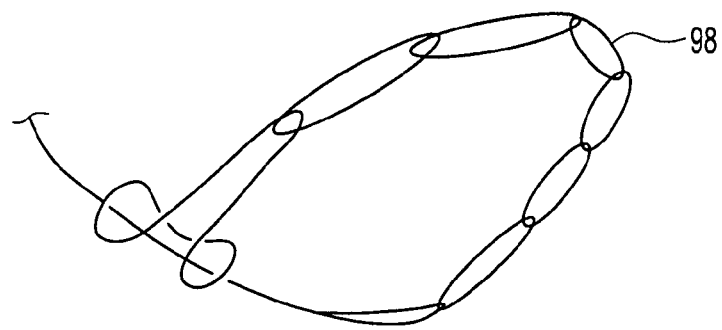
FIG. 18 illustrates a self-tightening suture chain configuration featuring an auxiliary disk anchoring device (shown in FIG. 19) according to the present invention.
Figure 19:
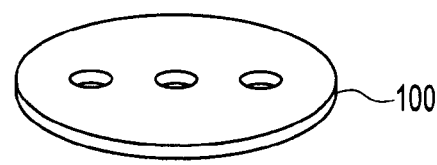
FIG. 19 illustrates an auxiliary disk anchoring device according to the present invention.
Figure 20:
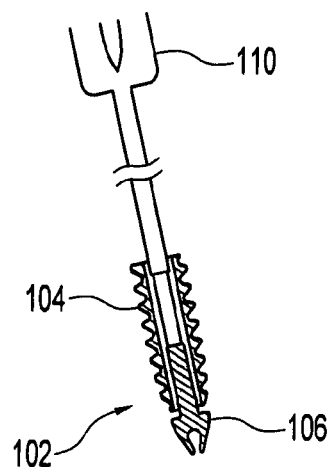
FIG. 20 illustrates a swivel suture chain anchor according to the present invention.

Other options for utilizing the suture chains of the present invention will become apparent to those of ordinary skill in the art. Referring to FIG. 18, for example, a self-tightening configuration in which suture chain 98 has been looped around itself is illustrated. Referring to FIG. 19, surface contact area of a suture chain construct can be expanded by threading a suture chain through a biocompatible disk 100. Single or multiple holes can be formed through disk 100 for accepting lengths of suture chain. The disk can be oblong to allow insertion through a narrow connection. This invention is not limited to a disk, per se. The invention includes other configurations such as rods or rectangles that will perform a similar function.

Referring to FIGS. 20, 21, 21A and 21B, another exemplary embodiment of the invention will be described in which a suture anchor 102 for securing a suture chain to bone features a swivel connection between a threaded body 104 and a detachable forked tip 106 (SwiveLock™ or swivel anchor). The rotatable attachment of forked tip 106 to threaded body 104 enables rotational insertion of anchor 102 without excessive twisting and knotting of a suture chain hooked by forked tip 106. Tip 106 is rotatable, i.e., swivels with respect to, body 104.

Referring more specifically to FIG. 21, and FIGS. 21A and 21B, a driver 110 is used to install anchor 102. Driver 110 features a cannulated tube 112 passing slidably and rotatably through a cannulated driver assembly 114. The tip 116 of cannulated tube 112 receives the proximal end forked tip 106, preferably via a snap fit, and is loaded into tube 112 by pulling on traction suture 118. Cannulated tube 112 maintains the rotational position of the tip 116 during insertion of the anchor. The outer surface of tube 112 has a polygonal shape to match and engage the inner cannulation of threaded anchor body 104.

Figure 22:
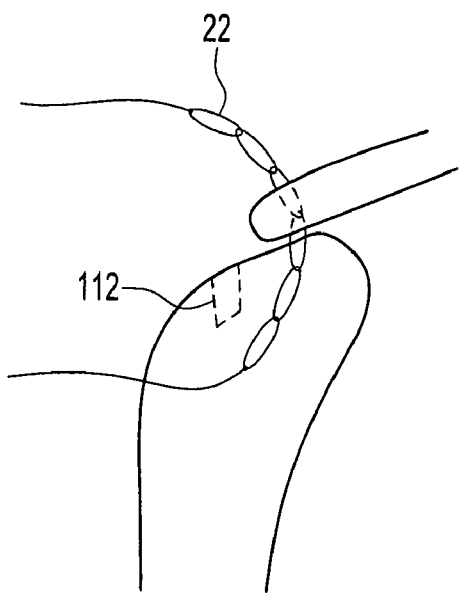
FIG. 22 illustrates a further step in shoulder repair according to the present invention.
Figure 23:
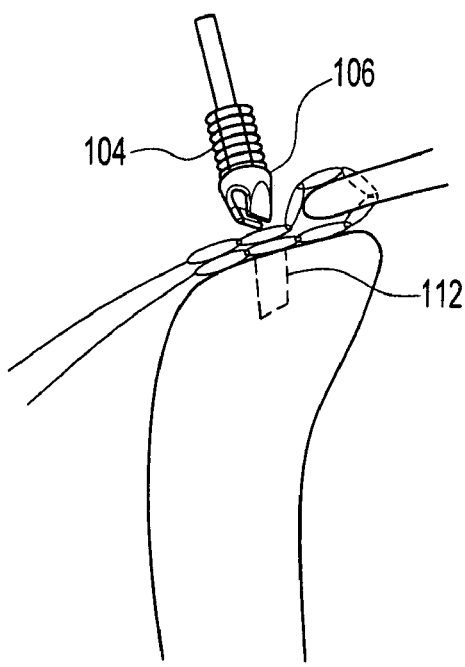
FIG. 23 illustrates a step in shoulder repair according to the present invention.
Figure 24:
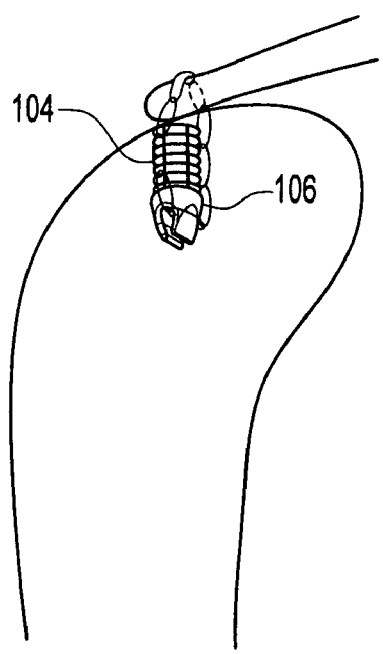
FIG. 24 illustrates a completed shoulder repair according to the present invention.

Referring in addition to FIGS. 22-24, during installation of swivel anchor 102, anchor body 104 is assembled onto operational end 122 of the driver 110. Anchor tip 106 is snapped into the distal end of cannulated tube 112. The forked anchor tip 106 is used to capture a suture chain 22 for installation into a pre-drilled hole in bone. Suture chain 22 has been laced through a shoulder tendon as shown in FIG. 22. Advantageously, the forked tip 106 can be inserted and retrieved from the pre-drilled hole 112 (FIG. 23) prior to installation of anchor body 104. Thus, adjustments to the tension on the suture chain can be made as necessary by changing the loop of the chain 22 captured by the forked anchor tip 106.

Once an appropriate construct is determined, the forked tip 106 and captured suture chain are held in place in the pre-drilled hole in bone by rotational insertion of threaded anchor body 104 as shown in FIG. 24. Forked tip 106 swivels with respect to threaded anchor body 104 so that tip 106 does not rotate as the anchor body is turned into bone. As explained above, the swivel suture anchor 102 may be employed as one of the two suture anchors 60, 70 in the method of knotless fixation described with reference to FIGS. 9-14.

Figure 25A:
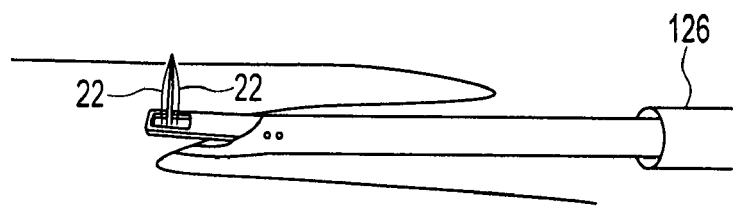
FIGS. 25A to 25G illustrate a method of knotless side-to-side suturing of U-shaped soft tissue defects using the suture chain of the present invention.
Figure 25B:
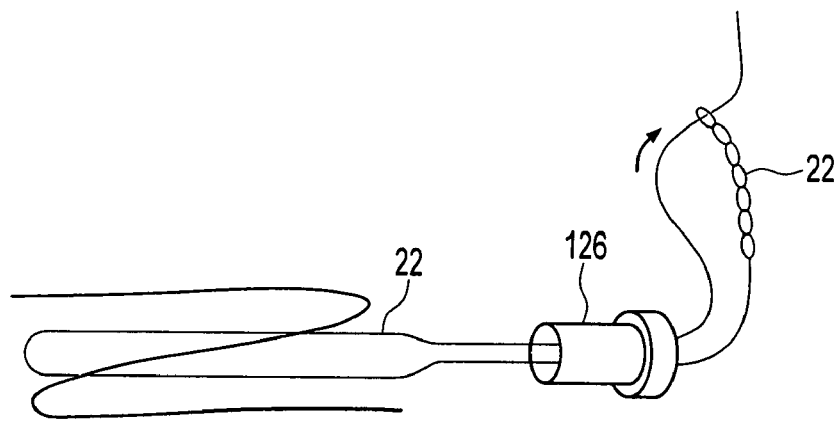
Figure 25C:
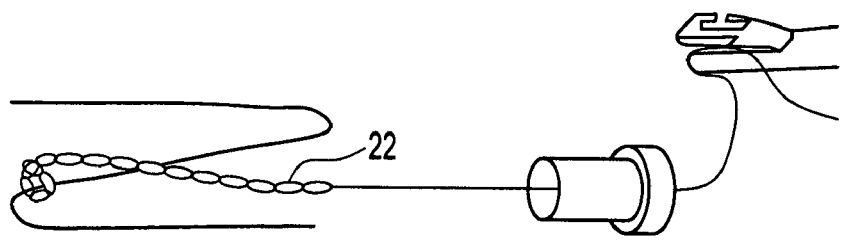
Figure 25D:
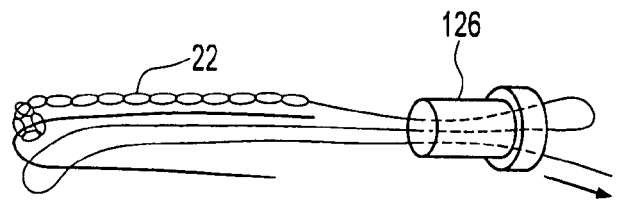
Figure 25E:
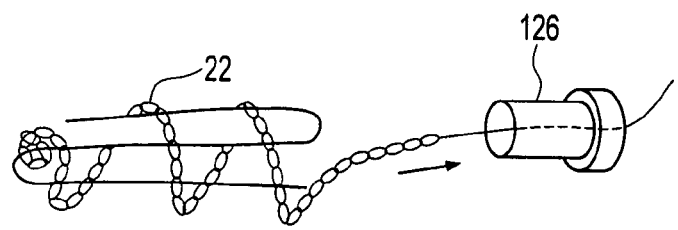
Figure 25F:
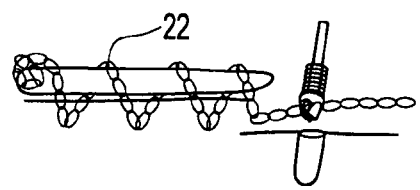
Figure 25G:
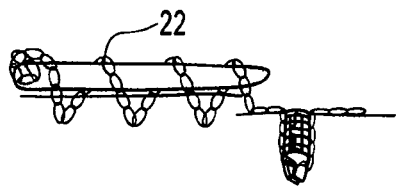

The suture chain of the present invention can also be used for knotless side-to-side suturing of U-shaped soft tissue defects (e.g., rotator cuff tears). Referring to FIG. 25A, the suture chain 22 of the present invention is passed through a U-shaped rotator cuff tear, near the apex of the tear, using a suture passing instrument such as the Scorpion sold by Arthrex, Inc. of Naples, Fla. As shown in FIG. 25B, outside of the cannula 126, the tail of the suture chain 22 is passed through the terminal link in the chain to fix the suture chain 22 to the apex of the tear. As shown in FIG. 25C, the tail of the suture chain 22 is then re-loaded into the Scorpion to pass through the opposite leaf of the U-shaped tear. Referring to FIG. 25D, the tail of suture chain 22 is passed through the rotator cuff, and the tail is then pulled to tighten suture chain 22 and pull the two leaves of the tear together. As shown in FIG. 25E, the above-described suture passage is repeated back and forth through the leaves of the rotator cuff. As shown in FIG. 25F, suture chain 22 is tensioned and secured to bone using an anchor, such as the swivel anchor described above, to complete the repair, as shown in FIG. 25G.

The above-described repair procedure, which can be performed with the suture chain of the present invention or regular suture strands, advantageously provides a knotless technique for margin convergence.

As described above, the suture chain of the present invention has application in surgical tissue repair, for example, in conjunction with one or more bone anchors. Tension on repair constructs is adjustable through selection of the chain link or links to be snagged by a bone anchor.

Other configurations include branched chains of two, three, or more individual chains radiating from a single intersecting link or several links. Each section of chain can be of uniform length with the others, or the chain sections can be a variety of lengths. Further configurations include strands or panels of two or more interlinked parallel chains forming a suturing device resembling chain mail. Multiple-ended suture chain configurations also are considered to be within the scope of the invention, without limitation.

FIGS. 26A to 26H illustrate a side view of a human shoulder of a patient undergoing a rotator cuff repair in accordance with an exemplary embodiment of a double row knotless tissue fixation of the present invention. According to this embodiment, footprint compression is enhanced and accelerated tendon healing to bone is achieved with minimal knot tying. As explained in more detail below, the double row repair consists of a medial row constructed with at least one suture anchor combined with knotless lateral fixation using at least one knotless fixation device and at least one strand of suture chain (Arthrex FiberChain). Preferably, the repair consists of a medial row constructed with two suture anchors (such as two Arthrex 5.5 mm Bio-Corkscrew® FT anchors) combined with knotless lateral fixation using two knotless fixation devices (such as two Arthrex SwiveLock™ or two Arthrex 3.5 mm PushLock™ anchors) and suture chain (FiberChain) of the present invention. The result is a quick, secure and low profile repair with excellent contact between tendon and bone.

First, the mobility of the tear is assessed using, for example, a tissue grasper such as the Arthrex KingFisher™ Suture Retriever/Tissue Grasper, to determine whether a U or L-shaped component exists. Where large tears extend to the superior aspect of the glenoid, margin convergence suturing is performed with FiberChain or FiberWire™ to reduce volume and strain on the repair. Subsequently, the length and width of the rotator cuff footprint is assessed and a bleeding bed for enhanced tendon to bone healing may be formed. This may be accomplished with a burr (such as a high-speed bur) to perform a light dusting of the greater tuberosity, or by using a chondro pick to microfracture the footprint and maximize vascular channels.

Pilot holes 232 (preferably two pilot holes 232) (FIG. 26A) are then prepared for two suture anchors 230 that will be inserted in the medial row through the percutaneous superolateral portal. A punch 210 (FIG. 26A) may be employed adjacent to the articular margin of the humerus and at about 45° angle ("deadman" angle) to form the two pilot holes. Tapping may be occasionally necessary.

Figure 26:
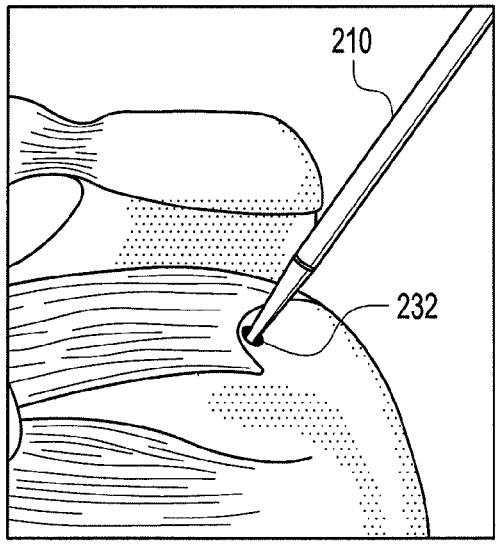
FIGS. 26A to 26H illustrate another method of knotless suturing of soft tissue using the suture chain of the present invention.
Figure 26:
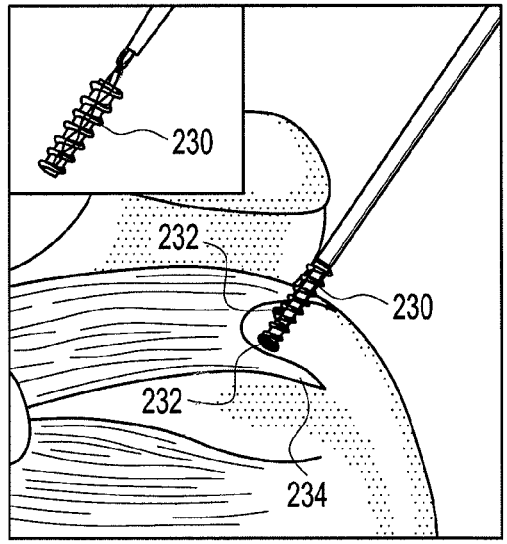
Figure 26:
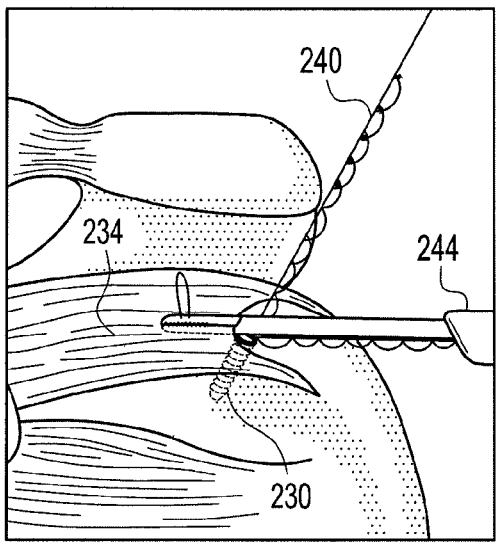
Figure 26:
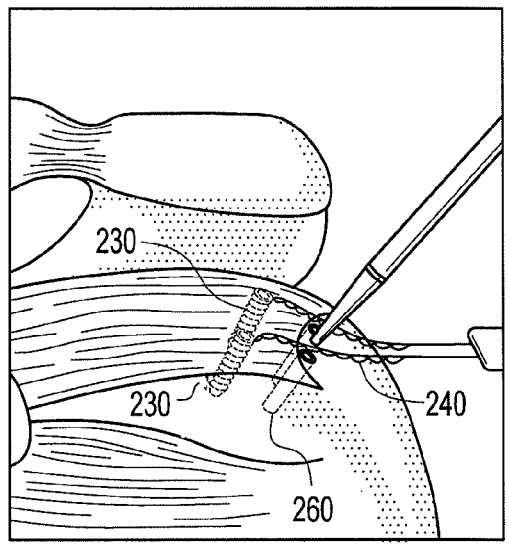
Figure 26:
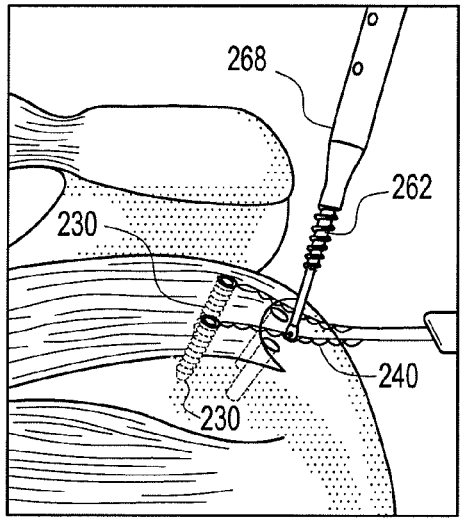
Figure 26:
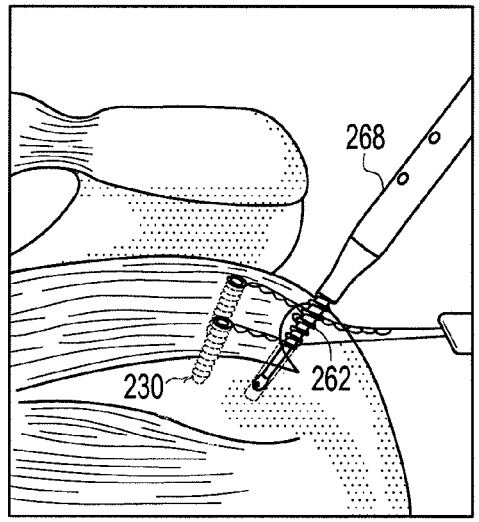
Figure 26:
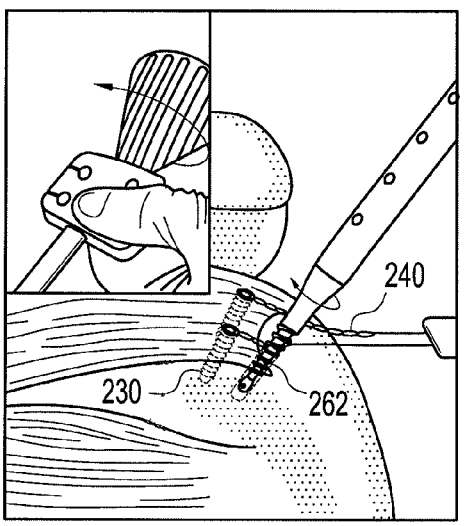
Figure 26:
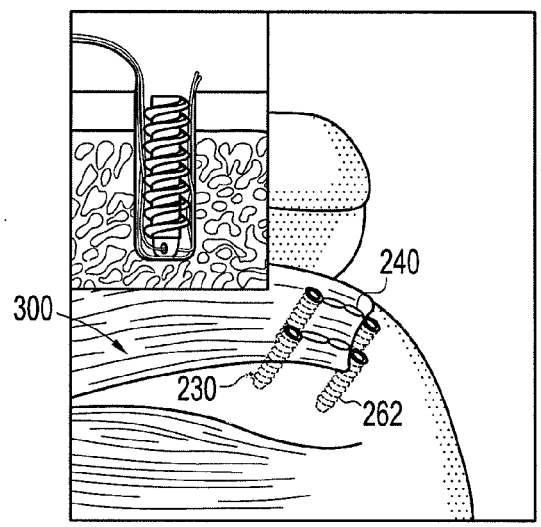

Subsequent to the formation of the pilot holes, and as shown in FIG. 26B, a suture anchor 230 is placed in the pre-formed hole 232. As shown in FIG. 26B, two suture anchors 230 are placed in the two pre-formed holes 232 in a medial row. These anchors assure full contact of the detached tendon 234 along the medial footprint of the greater tuberosity. In an exemplary embodiment, at least one of the two suture anchors is a fully-threaded bioabsorbable suture anchor having a loop inserted into the suture anchor, and as disclosed and described in U.S. patent application Ser. No. 11/224,060, filed on Sep. 13, 2005 and entitled "Fully-Threaded Bioabsorbable Suture Anchor," the disclosure of which is hereby incorporated by reference in its entirety.

In a preferred embodiment, suture anchors 230 have a flexible suture chain 240 (for example, FiberChain 240) pre-loaded on the suture anchor and attached to a proximal end 242, as illustrated in FIG. 26C.

Using a suture retriever instrument, the suture leader is retrieved from one of the suture chains 240 (FiberChain 240) through the lateral portal and is loaded onto a suture passer instrument 244 (for example, a Scorpion Suture Passer™). The suture leader of the FiberChain 240 is passed approximately 15 mm from the free margin of the tendon 234. This step is repeated for the second FiberChain 240. When large tears are present, and if desired, additional suture strands may be used to obtain additional medial fixation.

Referring now to FIG. 26D, once the medial row is formed, both FiberChain suture ends are retrieved through the lateral portal and tension is applied to them to bring the cuff into contact with the medial portion of the footprint. The tip of the cannula may be used to push the tendon against the footprint. Subsequently, through a percutaneous superolateral portal, two bone sockets 260 (two pilot holes 260) are formed for the lateral row comprising knotless fixation devices 262. The two bone sockets 260 may be formed using a punch, for example. In an exemplary embodiment, at least one of the two knotless fixation devices 262 is a fixation device such as an Arthrex SwiveLock™ anchor or an Arthrex PushLock anchor. Preferably, these two bone sockets are adjacent the lateral margin of the cuff when the cuff is appropriately tensioned by the two previously placed FiberChains.

As illustrated in FIG. 26E, the SwiveLock™ anchor 262 is introduced through the percutaneous superlateral portal and the third link from the free margin of the rotator cuff is captured. Each link in the FiberChain is about 6 mm in length. Since the total length of the SwiveLock anchor is about 18 mm, capturing the third link from the edge of the cuff edge typically positions the cuff directly at the edge of the bone socket and tensions the FiberChain and the rotator cuff segment that it spans, when the inserter tip pushes the FiberChain to the bottom of the bone socket 260.

Reference is now made to FIG. 26F. Once the desired FiberChain link is captured, the driver 268 is then advanced into the bone socket 260 and the FiberChain is pushed toward the bottom of the bone socket 260 until the anchor body contacts the bone. Tissue tension is evaluated. If it is determined that the tension is not adequate, the driver 268 can be backed out and the tension readjusted. In this instance, the driver 268 is removed from the bone socket by pulling on the free end of the FiberChain (to release any wedging of the swivel tip) at the same time the inserter is withdrawn. Subsequently, the adjacent (more proximal) link is captured. If the tension is too great to fully insert the driver to the bottom of the socket, the driver is removed and the adjacent, more distal link is captured. The driver is then reinserted to the base of the bone socket.

As shown in FIG. 26G, the screw is advanced by holding the thumb pad as the inserter handle is turned clockwise. When the implant is fully seated, the shaft of the forked swivel tip is fully engaged by the body of the screw-in portion of the anchor to optimize the stability of the SwiveLock™ anchor. The tip retention suture is unwound from the cleat at the back of the driver handle and the driver is removed. One limb of the retention suture is pulled to fully remove it from the implant.

The steps described above with reference to FIGS. 26E to 26G are subsequently repeated for the second SwiveLock™ anchor 262 to obtain the suturing arrangement 282 of FIG. 26H having double rows of fixation devices. The suturing arrangement 282, together with the two suture anchors 230 combined with knotless lateral fixation using the two knotless fixation devices 262 used in conjunction with FiberChain strands form exemplary repair system 300 (FIG. 26H) of the present invention.

Figure 27:
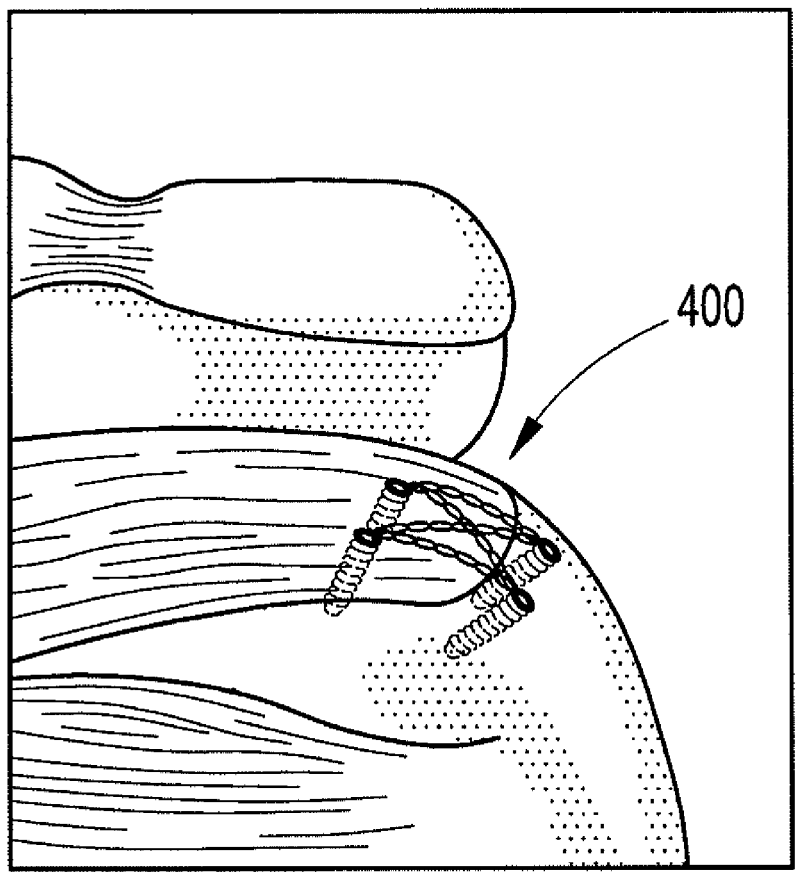
FIG. 27 illustrates another shared-load fixation using a method of knotless suturing of soft tissue using the suture chain of the present invention.

Although the invention has been described with reference to a particular suturing profile (such as the rectangular suture profile of the repair system 300 of FIG. 26H), the invention is not limited to this specific configuration and contemplates any suturing arrangements having various configurations and geometries, depending on the specifics of the repair site. For example, the double row fixation technique described above with reference to FIGS. 26A to 26H may be employed to form the criss-cross profile of FIG. 15, or the profile of FIG. 17, or the suturing profile of exemplary repair system 400 of FIG. 27. Thus, the invention is directed to any repair system including at least a portion of a FiberChain strand extending at least between one fixation device of a first row and at least one fixation device of a second row, in any pattern or configuration (such as X-shaped configuration, rectangular configuration, triangular configuration, trapezoidal configuration, regular polygonal configuration or irregular polygonal configuration, among many others). The suturing profile of a multi-pass structure secures a low profile repair with a shared-load fixation using the suture chain, and with excellent contact between tendon and bone.

The knotless fixation devices advantageously provide minimal knot-tying. The use of such fixation devices in conjunction with the FiberChain strands of the invention also minimizes loosening of the sutures—a tight suturing assembly results from the loops being pushed into a pilot hole on the lateral row and held tightly by an anchors.

In other embodiments of the present invention, a flexible elongated member, such as suture and/or tape, may be employed in conjunction with the FiberChain strands to further improve tissue compression and fixation in the anchors. Preferably, the tape, such as the suture tape disclosed in U.S. Patent Application Publication No. 2005/0192631, incorporated by reference herein, is braided and rectangular-like in cross-section. According to another embodiment, an allograft or biological component may be used in addition to the FiberChain strand or suture or suture tape. The allograft or biological component may be comprised of tendon or pericardium, for example, which provide an improved tissue repair. In yet additional embodiments, any combination of suture, suture tape, and allograft or biological component may be employed in addition to the FiberChain strand, depending on the characteristics of the specific surgical repair and/or as desired.

According to yet additional embodiments of the present invention, the repair system 300 of the present invention (illustrated in FIG. 26H and described above with specific reference to the two suture anchors 230 combined with knotless lateral fixation using the two knotless fixation devices 262 and the FiberChain strand forming multiple passes) may be further employed in conjunction with allograft or porous collagen material that may be optionally hydrated with bone marrow aspirate. In this embodiment, an implant material such as porous collagen material (BioSponge™) or tendon allograft (AlloBridge™) may be provided arthroscopically (preferably under the tissue or above the tissue) prior to implanting the lateral row of the repair system.

The porous collagen material (BioSponge™) or tendon allograft (AlloBridge™) can be readily hydrated or impregnated with a hydrating solution comprising aspirated bone marrow. The hydrating solution may consist essentially of bone marrow, preferably consisting essentially of autogenous bone marrow. Alternatively, the hydrating solution may comprise additional elements, such as various growth factors such as hyaluronic acid, antiseptics and/or antibiotics and medicine materials, in addition to or in lieu of the bone marrow. The BioSponge™ or AlloBridge™ impregnated or hydrated with bone marrow can act as carrier of bone marrow at the repair site, the bone marrow promoting a biological response to damaged tissue and reinforcing the repair of such damaged tissue. The implanted material may be provided at various locations of the repair site (for example, above the rotator cuff ligament, under the rotator cuff ligament, or extending from the rotator cuff ligament of the repair system 300 of FIG. 26(H)) depending upon the characteristics of the repair site and of the damaged tissue.

During the surgical repair, the bone marrow aspirate provides a cell suspension that may be readily processed intraoperatively for immediate implantation. According to an exemplary embodiment, the bone marrow aspirate may be withdrawn from the iliac crest or may be aspirated from the femur or humerus. Once the bone marrow is aspirated with a syringe, for example, from an aspirate region such as the humeral head, the BioSponge™ or AlloBridge™ is hydrated with the bone marrow and then the hydrated BioSponge™ or AlloBridge™ is provided arthroscopically (for example, under the tissue) prior to implanting the lateral row implants of repair system 300 of FIG. 26H. Alternatively, or additionally, bone marrow aspirate may be injected directly or localized to a repair site, to facilitate healing.

FIGS. 28A to 28H illustrate another embodiment of the present invention, according to which knotless single row repair system 500 (FIG. 28H) of the invention may be employed with or without the allograft or porous collagen material that may be optionally hydrated with bone marrow aspirate (as described above).

FIGS. 28A to 28H illustrate a side view of a human shoulder of a patient undergoing a rotator cuff repair in accordance with an exemplary embodiment of a single row knotless tissue fixation of the present invention. According to this embodiment, footprint compression is also enhanced and accelerated tendon healing to bone is achieved with minimal knot tying. As explained in more detail below, the single row repair consists of a row (or a plurality of rows) constructed with a knotless fixation device and at least one strand of suture chain (Arthrex FiberChain). Preferably, the repair consists of a fixation device (such as Arthrex SwiveLock™ or Arthrex 3.5 mm PushLock™ anchor) and the FiberChain of the present invention described above. The result is a quick, secure and low profile repair with excellent contact between tendon and bone.

First, and with reference to FIG. 28A, the mobility of the tear is assessed using, for example, a tissue grasper such as the Arthrex KingFisher™ Suture Retriever/Tissue Grasper, to determine whether a U or L-shaped component exists. Where large tears extend to the superior aspect of the glenoid, margin convergence suturing is performed with FiberChain or FiberWire™ to reduce volume and strain on the repair. Subsequently, the length and width of the rotator cuff footprint is assessed and a bleeding bed for enhanced tendon to bone healing may be formed. This may be accomplished with a burr (such as a high-speed bur) to perform a light dusting of the greater tuberosity, or by using a chondro pick to microfracture the footprint and maximize vascular channels.

Referring now to FIG. 28B, the nonlinked, free end of the FiberChain 240 is passed through the rotator cuff 234 using a suture passing instrument 244 (for example, a Scorpion Suture Passer) through a cannula (for example, a 5.75 mm Crystal Cannula®). The suture is retrieved through the same cannula.

Reference is now made to FIG. 28C. Free end 240*a* of the FiberChain 240 is passed through the terminal link at its opposite end. Cinch the loop down by pulling on the free end 240*a* of the FiberChain 240. The tip of the cannula (for example, Crystal Cannula) may be used to help seat the FiberChain loop securely against the rotator cuff. A suture retriever or grasper may be employed to ensure that the loop has been fully tightened. A second FiberChain may be passed through tissue by repeating the above steps.

The FiberChain 240 is used as a traction suture to determine the desired anchor location adjacent to the rotator cuff margin (FIG. 28D). A punch 210 (such as a 5.5 mm BioCorkscrew FT Punch) may be employed to punch bone socket 260 through a superolateral percutaneous portal. This step may be repeated for the second anchor.

Reference is now made to FIG. 28(E) and to the following steps: Both FiberChain ends are retrieved through the lateral portal. Anchor 262 (for example, a SwiveLock anchor) is introduced through the percutaneous superolateral portal, capturing the third link from the free margin of the rotator cuff. Each link in the FiberChain 240 is approximately 6 mm in length. Since the total length of the SwiveLock anchor is 18 mm, capturing the third link from the cuff edge will usually position the cuff directly at the edge of the bone socket and perfectly tension the FiberChain and the rotator cuff segment that it spans, when the inserter tip pushes the FiberChain to the bottom of the bone socket 260.

The driver is advanced into the bone socket 260 (FIG. 28(F)) and the FiberChain 240 is pushed toward the bottom of the socket until the anchor body 262 contacts the bone. The tissue tension is evaluated. If the tension is not adequate, the driver may be removed from the bone socket by pulling on the free end of the FiberChain (to release any wedging of the swivel tip) at the same time that the inserter is withdrawn. The adjacent (more proximal link) is captured. If the tension is too great to fully insert the driver to the bottom of the bone socket, the driver is removed and the adjacent, more distal link is captured. Then, the driver is reinserted to the base of the bone socket 260. The forked tip of the implant is preferably held to the driver with a 0 retention suture cleated at the proximal end of the driver.

Figure 28:
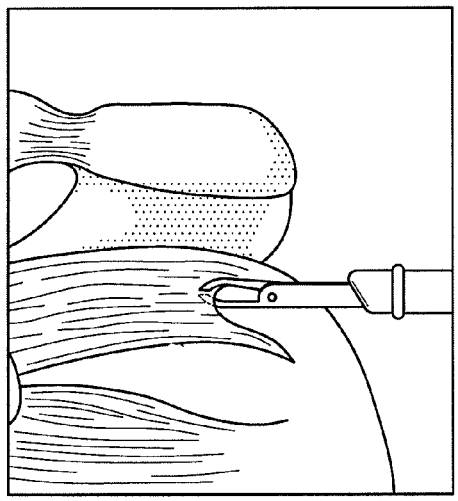
FIGS. 28A to 28H illustrate another method of single row knotless suturing of soft tissue using the suture chain of the present invention.
Figure 28:
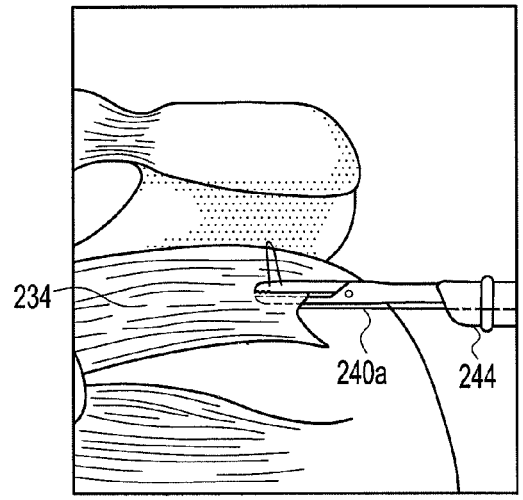
Figure 28:
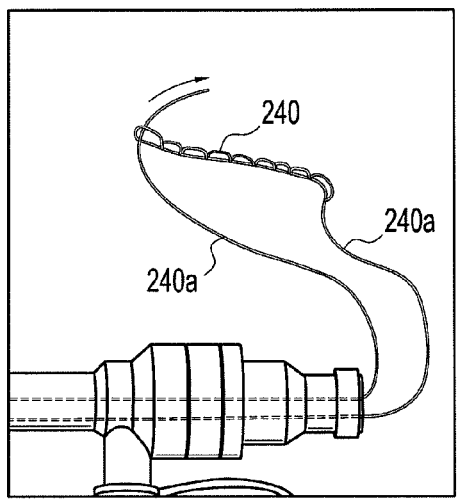
Figure 28:
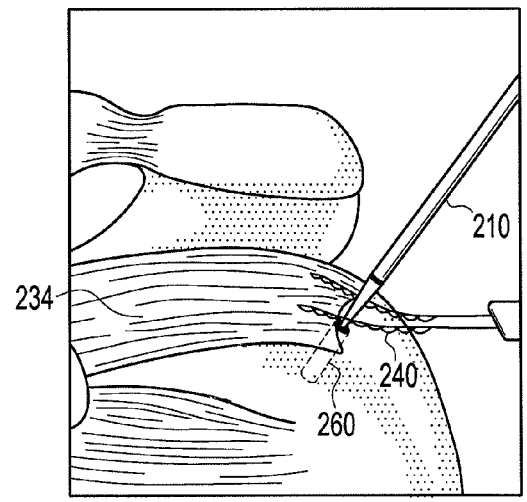
Figure 28:
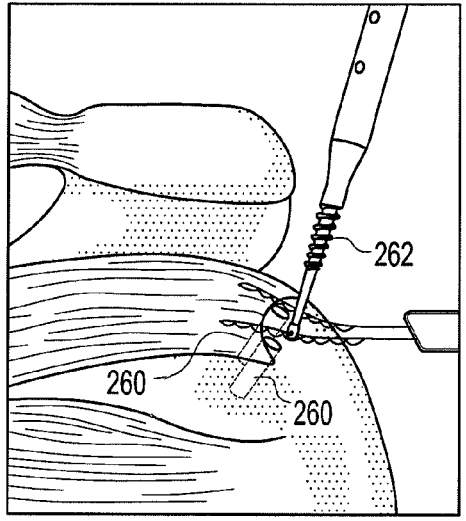
Figure 28:
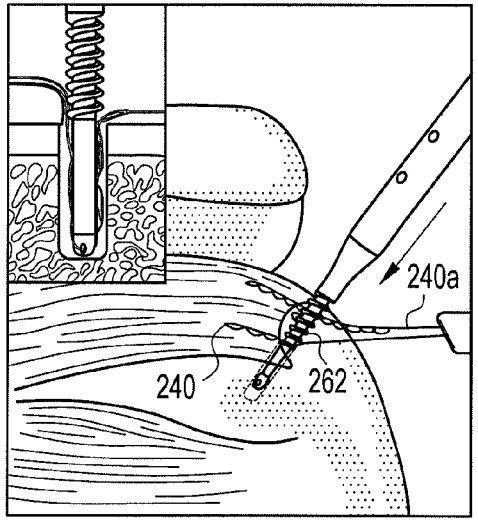
Figure 28:
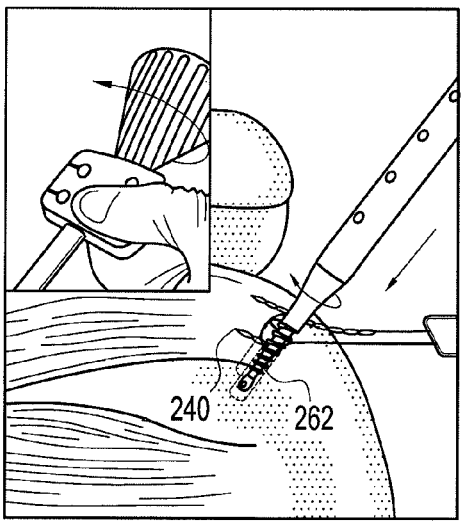
Figure 28:
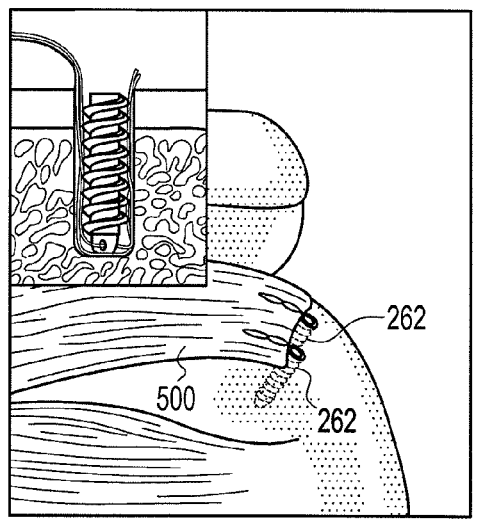

As shown in FIG. 28, the screw is advanced by holding the thumb pad as the inserter handle is turned clockwise. When the implant is fully seated, the shaft of the forked swivel tip is fully engaged by the body of the screw-in portion of the anchor to optimize the stability of the SwiveLock construct. The tip retention suture is unwound from the cleat at the back of the driver handle. The driver is removed. One limb of the retention suture is pulled to fully remove it from the implant. The insertion steps are repeated for the second SwiveLock 262 to obtain the final construct 500 (FIG. 28H). The free suture ends may be cut with an open ended instrument (for example, FiberWire Suture Cutter), for example, so that they are flush with the edge of the bone socket.

In other embodiments of the present invention, a flexible elongated member, such as suture and/or tape, may be employed in conjunction with the FiberChain strands of the single row repair system 500 to further improve tissue compression and fixation in the anchors, and as explained above with reference to the double row repair system 300. The single row repair system 500 may be further employed with an allograft or biological component which may be used in addition to the FiberChain strand or suture or suture tape, and as also detailed above with reference to the previously-described embodiments. In yet additional embodiments, the single row repair system 500 of the present invention (illustrated in FIG. 28H and described above) may be further employed in conjunction with allograft or porous collagen material that may be optionally hydrated with bone marrow aspirate. In this embodiment, and as also explained above, an implant material such as porous collagen material (BioSponge™) or tendon allograft (AlloBridge™) may be provided arthroscopically (preferably under the tissue or above the tissue) and preferably prior to the formation of the single row of FiberChain of the repair system.

Although the present invention has been described above with reference to two single rows of FiberChain forming the repair system 500, the invention is not limited to this exemplary embodiments and contemplates repair systems having one single FiberChain row, or a plurality of single FiberChain rows, disposed in any geometry, configuration and shape over the repair site. The invention also contemplates repair systems where single FiberChain rows are employed in conjunction with additional rows of various flexible materials, such as suture of FiberWire, among others. The present invention further contemplates embodiments wherein the single row technique is combined with the double row technique, both described above, and further in conjunction with single or multiple FiberChain rows and/or with rows of flexible strands (such as suture or FiberWire strands).

Although the present invention has been described in relation to particular embodiments thereof, many other variations and modifications and other uses will become apparent to those skilled in the art. It is preferred, therefore, that the present invention be limited not by the specific disclosure herein, buy only by the appended claims.

What is claimed is:

1. A method of attaching soft tissue to bone, comprising:
    providing a first medial row constructed with a first plurality of fixation devices, wherein the at least one of the first plurality of fixation devices is an anchor;
    providing a second lateral row constructed with a second plurality of fixation devices, wherein the at least one of the second plurality of fixation devices is a knotless fixation device;
    providing a suture chain comprising a plurality of suture loops wherein at least one of the plurality of suture loops is formed by lacing an end of the suture through itself to form the loop, the suture chain being attached to the anchor of the first medial row; and
    securing the suture chain at an opposite end in a hole in bone by the knotless fixation device of the second lateral row.

2. The method of claim 1, further comprising the step of forming multiple passes of the suture chain over the soft tissue.

3. The method of claim 2, further comprising the step of providing an implant material adjacent to the multiple passes of suture chain.

4. The method of claim 3, wherein the step of providing an implant material further comprises:
    providing aspirate bone marrow;
    providing a material to be implanted in the vicinity of a repair site defined by at least the multiple passes of suture chain;
    hydrating the material with aspirate bone marrow to form the implant material; and
    securing the implant material at the repair site.

5. The method of claim 4, wherein the implant material is collagen or allograft.

6. The method of claim 5, wherein the implant material is porous collagen impregnated with autogenous bone marrow.

7. The method of claim 5, wherein the implant material is tendon allograft impregnated with autogenous bone marrow.

8. The method of claim 1, wherein the multiple passes have a criss-cross configuration, an X-shaped configuration, a rectangular configuration, a trapezoidal configuration, a regular polygonal configuration or an irregular polygonal configuration.

9. The method of claim 1, further comprising the step of capturing a loop of the suture chain prior to the step of securing the suture chain in the hole in bone.

10. The method of claim 1, wherein at least one of the plurality of suture loops has a perimeter which is approximately equal to that of another of the plurality of suture loops.

11. The method of claim 1, wherein the soft tissue is rotator cuff tendon or shoulder ligament.

* * * * *